United States Patent

Baumann

Patent Number: 5,470,355
Date of Patent: Nov. 28, 1995

[54] ORGANIC COMPOUNDS

[75] Inventor: Hans-Peter Baumann, Ettingen, Switzerland

[73] Assignee: Sandoz Ltd., Basle, Switzerland

[21] Appl. No.: 191,346

[22] Filed: Feb. 3, 1994

Related U.S. Application Data

[63] Continuation of Ser. No. 759,278, Sep. 13, 1991, abandoned, which is a continuation of Ser. No. 570,927, Aug. 21, 1990, abandoned, which is a continuation of Ser. No. 376,329, Jul. 6, 1989, abandoned, which is a continuation of Ser. No. 834,179, Feb. 26, 1986, abandoned, which is a continuation-in-part of Ser. No. 678,251, Dec. 5, 1984, abandoned.

[30] Foreign Application Priority Data

Dec. 5, 1983 [DE] Germany .................... 33 43 949.4

[51] Int. Cl.⁶ .................... C09B 67/40; C07C 305/12
[52] U.S. Cl. .................... 8/587; 558/37; 8/589
[58] Field of Search .................... 558/37; 8/587, 8/589

[56] References Cited

U.S. PATENT DOCUMENTS 3,919,429  11/1975  Grossmann et al. .

FOREIGN PATENT DOCUMENTS 28756    7/1983  European Pat. Off. .
7407582  1/1974  Japan .
1425391  2/1976  United Kingdom .
1388251  3/1976  United Kingdom .

*Primary Examiner*—Nicky Chan
*Attorney, Agent, or Firm*—Robert S. Honor; Carl W. Battle; Michael P. Morris

[57] ABSTRACT

Compounds of formula I

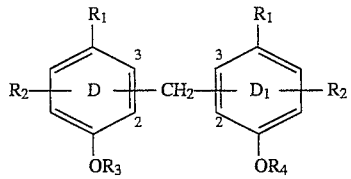

in which $R_1$ is isooctyl, nonyl or dodecyl, $R_2$ is H or $-SO_3R_6$, $R_3$ is $-(A-O)_m R_5$ where each A, independently, is $-C_2H_4-$, $-C_3H_6-$ or $-C_4H_8-$, $R_4$ is $-(B-O)_n R_5$ where each B, independently, is $-C_2H_4-$, $-C_3H_6-$ or $-C_4H_8-$, $R_5$ is H or $-SO_3R_6$, provided that at least one $R_5$ is $-SO_3R_6$, $R_6$ is H, an alkali metal, an equivalent of an alkaline earth metal or optionally substituted ammonium, m is 1, 2 or 3 and n is 0, 1 or 2, provided that m+n is at most 4, when n=0 then $R_5$ is H and m=1, when only one group $R_5$ is $-SO_3R_6$ and n=1 or 2 then both $R_2$'s are H, are useful as emulsifying and dispersing agents, especially as dyeing or printing assistants for dyeing or printing a substrate dyeable with anionic or disperse dyes.

6 Claims, No Drawings

ORGANIC COMPOUNDS

This is a continuation application of application Ser. No. 07/759,278 filed on 13 Sep. 1991, abandoned, which in turn is a continuation of application Ser. No. 07/570,927 filed 21 Aug. 1990, abandoned, which in turn is a continuation of application Ser. No. 07/376,329, filed 6 Jul. 1989, abandoned which in turn is a continuation of application Ser. No. 06/834,179, filed 26 Feb. 1986, abandoned, which in turn is a continuation-in-part application of Ser. No. 06/678,251 filed 5 Dec. 1984, abandoned.

The present invention relates to bis-phenol-methane derivates useful as dispersing or emulsifying agents.

According to the invention, there are provided compounds of formula I

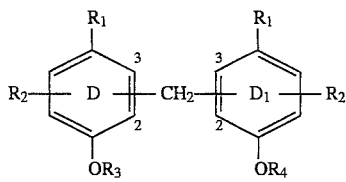

in which each $R_1$, independently, is isooctyl, nonyl or dodecyl each $R_2$, independently, is hydrogen or —$SO_3R_6$ $R_3$ is —(A—O)$_m$$R_5$ where each A, independently, is —$C_2H_4$—, —$C_3H_6$— or —$C_4H_8$—

$R_4$ is —(B—O)$_n$$R_5$ where each B, independently, is —$C_2H_4$—, —$C_3H_6$— or —$C_4H_8$— each $R_5$, independently, is hydrogen or —$SO_3R_6$, provided that at least one $R_5$ is —$SO_3R_6$ each $R_6$, independently, is hydrogen, an alkali metal, an equivalent of an alkaline earth metal, ammonium or substituted ammonium, m is 1, 2 or 3, and n is 0, 1 or 2 with the provisos that the total sum m+n is at most 4, that when n=0 then $R_5$ in $R_4$ is hydrogen and m is 1 and that when only one group $R_5$ is —$SO_3R_6$ and n=1 or 2 then both $R_2$'s are hydrogen.

In the compounds of formula I, the symbols $R_1$ are preferably identical and are more preferably nonyl.

When n=0 or each $R_3$ and $R_4$ contain a terminal —$SO_3R_6$ group, one symbol $R_2$ is preferably hydrogen and the other is hydrogen or —$SO_3R_6$, preferably —$SO_3R_6$.

$R_3$ or $R_4$ may also be a mixed chain containing —$C_2H_4$—, —$C_3H_6$— and/or —$C_4H_8$— in any sequence. When n=1 or 2, $R_3$ and $R_4$ may contain an identical or different alkylene oxide addition chain. Preferably $R_3$ is distinct from $R_4$.

—$C_3H_6$— as $R_3$ or $R_4$ is 1,2-propylene. —$C_4H_8$— as $R_3$ or $R_4$ is 1,2- or 2,3-butylene. Preferably each A or B is ethylene or 1,2-propylene.

$R_3$ is preferably

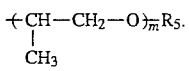

$R_4$ is preferably

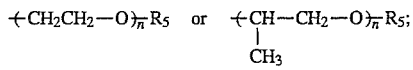

more preferably n is 0 and in this case $R_4$ is H and m is 1.

Substituted ammonium as $R_6$ is an ammonium substituted by up to four $C_{1-4}$alkyl or up to three β-, γ- or ω-hydroxy-$C_{2-4}$alkyl, e.g. dimethylammonium, trimethylammonium or mono-, di- or tri-ethanolammonium, or cycloammonium. The latter is an ammonium group incorporated in a cyclic system which may contain further hetero atoms. When $R_6$ is cycloammonium it is preferably morpholinium.

$R_6$ is preferably hydrogen, sodium, potassium, ammonium or monoethanolammonium, more preferably monoethanolammonium. The $R_6$'s symbols are preferably all identical in the molecule.

The sum m+n is preferably 1 or 2, particularly 1.

In the compounds of formula I, the bridging methylene group may be attached in the 2,3-positions on rings D and $D_1$. Preferably the bridging methylene group is attached in the 2,2-position on rings D and $D_1$.

When $R_2$ is —$SO_3R_6$, it may be attached in any of the remaining free positions on ring D and/or ring $D_1$. When only one $R_2$ is —$SO_3R_6$ and n=0, the —$SO_3R_6$ radical is then preferably attached on the ring bearing the —$OR_4$, i.e. OH, radical.

Preferred compounds of formula I are those in which the $R_1$'s are as defined above, at least one $R_2$ is hydrogen, $R_3$ is —(CH$_2$CH$_2$—O)$_m$$R_5$ or —(C$_3$H$_6$—O$R_5$, $R_4$ is —(CH$_2$CH$_2$—O)$_n$$R_5$ or —(C$_3$H$_6$—O)$_n$$R_5$, at least one $R_5$ is —$SO_3R_6$, the $R_6$'s are hydrogen, sodium, potassium, ammonium or monoethanolannonium, m is 1, 2 or 3 and n is 0, 1 or 2, the total sum m+n being 1, 2, 3 or 4 with the above indicated provisos. Preferably the $R_1$'s are nonyl.

More preferred compounds of formula I are those in which the $R_1$'s are nonyl, one $R_2$ is hydrogen and the other is —$SO_3R_6$, $R_3$ is

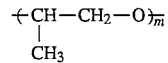

where $R_5$ is —$SO_3R_6$, $R_4$ is —(B—O)$_n$$R_5$ where n=0 and $R_5$ is hydrogen, the $R_6$'s are hydrogen, sodium, potassium, ammonium or monoethanolammonium, and m is 1.

Most preferably the methylene bridging rings D and $D_1$ is attached in the 2,2-position.

The compounds of formula I are prepared by reacting a compound of formula II

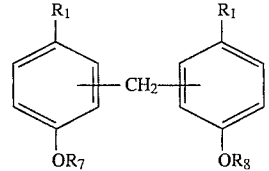

in which $R_7$ is —(A—O)$_m$H $R_8$ is —(B—O)$_n$H and A, B, $R_1$, m and n are as defined above, provided that the total sum m+n is at most 4 and when n is 0 then m is 1, or a mixture thereof, with sulphur trioxide, sulphuric acid, oleum, aminosulphonic acid or chlorosulphonic acid in a mole ratio of 1:1.5–2.5 and, where desired, converting the free sulphonic acid group(s) into an alkali metal, alkaline earth metal, ammonium or substituted ammonium salt form.

The sulphation/sulphonation reaction is carried out in accordance with known methods within a temperature range from 0° to about 150° C. In this reaction, the terminal hydroxy group of the glycolic oxide chain(s) is first sulphated. If the sulphating agent is present in excess, then the benzene rings are sulphonated. Depending on the presence of one or two of such terminal glycolic hydroxy groups and on the amount of sulphur trioxide, oleum, sulphuric acid or amino- or chlorosulphonic acid used, there can be produced compounds of formula I containing one or two sulphuric acid semi-ester groups (one $R_5$ or both $R_5$'s) and, provided that no unsulphonated glycolic hydroxy group is present, up to two sulphonic acid groups on the benzene rings and mixtures thereof.

The compounds of formula I are preferably obtained in the form of a mixture particularly when they are ring-sulphonated.

Chlorosulphonic acid is preferred as a sulphating agent and optionally as a sulphonating agent.

The compounds of formula I in free acid form can be converted into the salt form by neutralization with an organic or inorganic base, e.g. an alkali metal hydroxide, an alkali earth metal hydroxide, ammonia or a basic amine. When the compounds of formula I are obtained in the form of a mixture, they may be separated and purified according to known methods. Preferably the compounds of formula I are used in the form of a mixture such as produced.

The compounds of formula II may be prepared by analogy with known methods, e.g. by condensing an iso-octyl-, nonyl- or dodecylphenol with formaldehyde at a mole ratio 2:1, preferably in the presence of an acid catalyst, e.g. a strong organic or inorganic acid such as oxalic acid, hydrochloric acid or sulphuric acid. The resulting binuclear compounds are then oxyalkylated with 1–4 moles ethylene oxide, 1,2-popylene oxide and/or 1,2- or 2,3-butylene oxide. The oxyalkylation may be carried out according to known methods, conveniently in the presence of a catalyst, e.g. NaOH or KOH, either without pressure or in an autoclave. When the oxyalkylation is carried out using ethylene oxide and 1,2-propylene oxide, the two alkylene oxides may be added either in the form of a mixture or in alternation. When the sum m+n>2, the compounds of formula II are preferably obtained in the form of a mixture of oxyalkylated compounds.

The compounds of formula I and their mixtures are useful emulsifying and dispersing agents. They are particularly suitable as dyeing or printing assistants, e.g. as leveling agents.

Dyeing and printing in the presence of compounds of formula I as leveling agents may be carried out in accordance with known methods for dyeing or printing textile substrates dyeable with an anionic or disperse dyestuff. The amount of compound of formula I employed in the dyeing or printing paste will depend on the textile substrate, the dyestuff employed, the pH of the bath and the treatment time. In general suitable amounts are in the range of from 0.02 to 20% by weight, preferably 0.1 to 15% by weight based on the weight of the substrate.

The preferred substrates are those comprising natural or synthetic polyamides, polyesters or cellulose acetate or mixtures thereof. The compounds of formula I result in level dyeings especially in the case of stripy nylon.

The compounds of formula I may also be used as assistants for dyeing leather. They are also valuable dispersing or emulsifying agents for the preparation of agrochemical formulations or for use in the paper industry.

When the compounds of formula I are employed as dispersing or emulsifying agents, they are employed in accordance with known methods and in conventional amounts.

The compounds of formula I in which at least one $R_2$ is $—SO_3R_6$ are also useful as stabilizing agents for peroxides in peroxide bleaching. They are particularly suitable for stabilizing hydrogen peroxide, preferably in admixture with a silicate.

The compounds of formula I may have a low solubility in water depending on their sulphation and sulphonation rate and their salt form. For example, sodium salts are less hydrosoluble than the monoethanolannonium salts.

The compounds of formula I are conveniently used in admixture with a co-surfactant and such compositions form also part of the invention. Suitable co-surfactants include aliphatic $C_{3-6}$ alcohols and their ethers, e.g. isopropanol, cyclohexanol, butanol, isobutanol, 2-methyl-2,4-pentanediol, 1-butoxy-2-hydroxyethane, butyleneglycol, butyldiglycol and mixtures thereof. The weight ratio of the compound of formula I to the co-surfactant may vary from 3:17 to 17;3, preferably from 3:2 to 4:1. Preferred co-surfactants are butanol, isobutanol, butyleneglycol or butyldiglycol. Such mixtures are readily dilutable with water.

The present invention further provides a composition comprising a compound of formula I or a mixture of compounds of formula I, a co-surfactant and water. Preferred compositions are those containing from 15 to 30% by weight of a compound of formula I or a mixture of compounds of formula I, 5 to 30% by weight of a co-surfactant and water up to 100%.

The following Examples further serve to illustrate the invention. In the Examples all parts are by weight and all temperatures are in degrees Centigrade.

EXAMPLE 1

880 (4M) Parts p-nonylphenol are put into a flask and heated with stirring and introduction of a nitrogen stream to 50°. There are then added a solution of 13.2 parts oxalic acid dihydrate in 8.4 parts demineralised water, 4.4 parts sodium dodecylbenzenesulphonate and, finally, portionwise 63.2 parts paraformaldehyde at such a rate that the temperature in the flask rises to 85°–125°. The resulting mixture is slowly heated to 120°–125° and the water contained in the mixture is removed by distillation at approx. 5 mm Hg. The mixture is further heated to 160° and stirred at this temperature for 3 hours. The resulting compound essentially corresponds to bis-(4-nonyl-2-phenol)methane. The vacuum is broken by feeding in nitrogen, 5 parts solid sodium hydroxide are slowly added to the mixture and, while the pressure is reduced to approx. 18 mm Hg, 264 parts ethylene oxide are introduced under the surface. Stirring is continued for one hour at 150°–170°.

584 Parts of the addition product obtained above are put into a flask. To this product are added 861 parts methylene chloride with stirring and the mixture is cooled to 2°–5°. 233 Parts chlorosulphonic acid are then added slowly to the mixture at such a rate that the temperature does not exceed 20°. The gaseous hydrogen chloride formed is absorbed by an aqueous sodium hydroxide solution. After completion of the chlorosulphonic acid addition, the resulting mixture is further stirred for about 3 hours, brought to room temperature and then added slowly to 190 parts monoethanolamine cooled to 2°–5°, at such a rate that the temperature does not exceed 20°. After further stirring for 2 hours at room temperature, the methylene chloride is distilled off at approx. 65° while reducing the pressure to 60 mm Hg.

There are obtained 590 parts of a product containing essentially the compound of formula $$\begin{array}{c} C_9H_{19} \quad\quad C_9H_{19} \\ \text{--CH}_2\text{--} \\ \text{OCH}_2\text{CH}_2\text{OSO}_3^{\ominus} \overset{\oplus}{\text{NH}_3}\text{CH}_2\text{CH}_2\text{OH} \\ \text{O(CH}_2\text{CH}_2\text{O)}_2\text{SO}_3^{\ominus} \ \overset{\oplus}{\text{NH}_3}\text{CH}_2\text{CH}_2\text{OH} \end{array}$$

The compound is mixed with 300 parts isobutanol and stirred at approx. 40° to give a clear solution.

Instead of the 190 parts monoethanolamine, equimolar amounts of di- or triethanolamine, morpholine or ammonia may be used for the neutralization to the salt form.

By following the same procedure but using the compounds of the Table in the indicated mole amounts, further compounds of formula I may be prepared. In each Example, the alkylphenol is reacted with formaldehyde at a mole ratio of 2:1, essentially in the ortho position to the phenolic hydroxy group. The resulting compounds of formula I are obtained in the form of a mixture.

TABLE

| Ex.No. | $R_1$ | Mole Alkyleneoxide | Mole Chlorosulphonic acid |
|---|---|---|---|
| 2 | Nonyl | 3 Propyleneoxide | 2 |
| 3 | Dodecyl | 3 Ethyleneoxide | 2 |
| 4 | Nonyl | 2 Ethyleneoxide | 2 |
| 5 | Nonyl | 1 Ethyleneoxide | 1.5 |
| 6 | Nonyl | 1 Propyleneoxide | 2.25 |
| 7 | Nonyl | 4 Ethyleneoxide | 2 |
| 8 | Nonyl | 4 Propyleneoxide | 2 |
| 9 | Nonyl | 3 Propyleneoxide | 2.5 |
| 10 | Nonyl | 1 Ethyleneoxide | 2 |
| 11 | Dodecyl | 2 Ethyleneoxide | 1.5 |
| 12 | Dodecyl | 2 Ethyleneoxide | 2 |
| 13 | Isooctyl | 2 Ethyleneoxide | 1.5 |
| 14 | Isooctyl | 2 Ethyleneoxide | 2 |
| 15 | Nonyl | 1 Propyleneoxide + 2 Ethyleneoxide | 2 |
| 16 | Nonyl | 2 Ethyleneoxide | 2.5 |
| 17 | Nonyl | 2 Propyleneoxide + 2 Ethyleneoxide | 2 |
| 18 | Nonyl | 2 Ethyleneoxide | 1.5 |
| 19 | Nonyl | 1 Propyleneoxide + 3 Ethyleneoxide | 2 |
| 20 | Nonyl | 3 Ethyleneoxide | 2.5 |
| 21 | Nonyl | 3 Ethyleneoxide | 1.5 |
| 22 | Nonyl | 1 Butyleneoxide | 2.25 |
| 23 | Nonyl | 1 Butyleneoxide | 2.5 |
| 24 | Nonyl | 1 Propyleneoxide | 2.5 |

The resulting compounds are then admixed with isobutanol as disclosed in Example 1.

Application Example A

100 Parts stripy nylon 6 fabric are added to 1500 parts of a dyebath containing monosodium phosphate and tetrasodium pyrophosphate to adjust the bath pH to 8

0.6 parts of the dye C.I. Acid Red 57, and 2.0 parts of the product of Example 6 in monoethanolamine salt form and treated with this dyebath at the boil for 90 minutes. The substrate is then rinsed and dried. A level red dyeing is obtained.

By repeating the procedure but replacing the dyestuff C.I. Acid Red 57 by C.I. Acid Blue 80, C.I. Acid Orange 148, C.I. Acid Orange 127, the same good results are obtained.

Application Example B

100 Parts of a 60:40 nylon 6/wool blended fabric are added to 3000 parts of a dyebath adjusted to pH 8 and containing 1 part of the dyestuff C.I. Acid Blue 80 and 4 parts of the compound of Example 1 in the monoethanolamine salt form, and dyed at 98° for 90 minutes. The substrate is then rinsed and dried. An excellent level deep blue dyeing is obtained.

In the above procedure, the compound of Example 1 may be replaced by the product of Example 8 or 10 in an equivalent amount.

By repeating the procedure but replacing the dyestuff C.I. Acid Blue 80 by C.I. Acid Orange 145, C.I. Acid Orange 127, C.I. Acid Red 299, C.I. Acid Red 57, C.I. Acid Red 263, C.I. Acid Violet 48, C.I. Acid Blue 126 or C.I. Acid Blue 271, the same good results are obtained.

Application Example C

A polyester fabric is dyed with 0.5% of the dyestuff C.I. Disperse Red 13 with the addition of 2 g/l ammoniumsulphate and 2 g/l of the product of Example 6 at pH 5 (adjusted with formic acid). The liquor to goods ratio is 20:1. The dyeing is effected at 130° for 20 minutes. The substrate is washed and rinsed. A level dyeing is obtained.

In Examples A–C, the compound of formula I is used in admixture with isobutanol as disclosed in Example 1. The isobutanol may also be replaced by an equivalent amount of butyldiglycol.

What is claimed is:

1. A compound of formula I $$\begin{array}{c} R_1 \quad\quad\quad R_1 \\ R_2 \text{---} D \text{---} CH_2 \text{---} D_1 \text{---} R_2 \\ OR_3 \quad\quad OR_4 \end{array} \quad I$$

in which each $R_1$, independently, is isooctyl, nonyl or dodecyl, each $R_2$, independently, is hydrogen or $-SO_3R_6$, $R_3$ is $-(A-O)_m R_5$ where each A, independently, is $-C_2H_4-$, $-C_3H_6-$, $C_4H_8-$, and the $R_5$ in $R_3$ is $-SO_3R_6$, $R_1$ is hydrogen, each $R_6$, independently, is hydrogen, an alkali metal, an equivalent of an alkaline earth metal, ammonium or substituted ammonium, and, m is 1, or a mixture thereof.

2. A compound according to claim 1, in which the $R_1$'s are isooctyl, nonyl or dodecyl, one $R_2$ is hydrogen and the other is $-SO_3R_6$, $R_3$ is

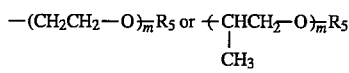

$R_4$ is hydrogen,
$R_5$ is $-SO_3R_6$,
$R_6$, independently, is hydrogen, sodium, potassium, ammonium or monoethanolammonium, and,
m is 1,
or a mixture thereof.

3. A compound according to claim 2 in which
the $R_1$'s are nonyl,
one $R_2$ is hydrogen and the other is $-SO_3R_6$,
$R_3$ is

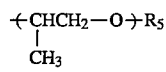

where $R_5$ is $-SO_3R_6$,
$R_4$ is hydrogen,
the $R_6$'s are hydrogen, sodium, potassium, ammonium or monoethanolammonium, or a mixture thereof.

4. A composition comprising:
   a compound according to claim 1 or a mixture thereof;
   a co-surfactant; and,
   water.

5. A composition according to claim 4 wherein the co-surfactant is an aliphatic $C_{3-6}$ alcohol or an ether thereof.

6. A composition according to claim 4 comprising per 100% by weight:
   15–30% by weight of a compound according to claim 1 or a mixture thereof;
   5–30% by weight of a co-surfactant; and,
   water.

* * * * *